(12) United States Patent
Browne et al.

(10) Patent No.: US 10,493,252 B2
(45) Date of Patent: Dec. 3, 2019

(54) URETHRAL BALLOON DILATOR CATHETER

(71) Applicant: Advanced Dilation Strategies, LLC, Cambridge, MA (US)

(72) Inventors: Brendan M. Browne, Cambridge, MA (US); Leonard N. Zinman, Burlington, MA (US)

(73) Assignee: Advanced Dilation Strategies, LLC, Cambridge, MA (US)

( * ) Notice: Subject to any disclaimer, the term of this patent is extended or adjusted under 35 U.S.C. 154(b) by 0 days.

(21) Appl. No.: 16/206,485

(22) Filed: Nov. 30, 2018

(65) Prior Publication Data

US 2019/0091453 A1 Mar. 28, 2019

Related U.S. Application Data

(63) Continuation of application No. 16/056,030, filed on Aug. 6, 2018, now Pat. No. 10,201,689.
(Continued)

(51) Int. Cl.
*A61M 29/02* (2006.01)
*A61M 25/10* (2013.01)
(Continued)

(52) U.S. Cl.
CPC ........ *A61M 29/02* (2013.01); *A61M 25/1011* (2013.01); *A61B 1/00082* (2013.01);
(Continued)

(58) Field of Classification Search
CPC .............. A61M 25/1011; A61M 25/00; A61M 25/0017; A61M 25/0021; A61M 25/007; A61M 25/10; A61M 25/1006; A61M 25/104; A61M 29/02; A61M 29/00; A61M 2025/1079; A61M 2025/0039; A61M 2025/0175; A61M 2025/1015; A61M 2025/1052; A61M 2210/166; A61M 16/04; A61M 27/00; A61B 17/0401; A61B 17/0487; A61B 2017/0409; A61B 2017/0414; A61B 2017/045;
(Continued)

(56) References Cited

U.S. PATENT DOCUMENTS 2,257,369 A 9/1941 Davis
4,423,725 A 1/1984 Baran et al.
(Continued)

OTHER PUBLICATIONS

Notice of Allowance, Examiner Initiated Interview Summary, and Office Action Appendix dated Nov. 26, 2018 for U.S. Appl. No. 16/056,030 (29 Pages).
(Continued)

*Primary Examiner* — Ryan J. Severson
*Assistant Examiner* — Mohamed G Gabr
(74) *Attorney, Agent, or Firm* — Brown Rudnick LLP

(57) ABSTRACT

A medical device for dilating urethral strictures comprises a urethral catheter disposed inside a slidable sheath. The device includes a localizing balloon and one or more dilating balloons capable of expanding radially outward to mechanically expand the urethral stricture. In certain embodiments, the device is adjustable in order to position the location of the one or more dilating balloons of the device relative to the urethral stricture of a patient.

23 Claims, 9 Drawing Sheets

Related U.S. Application Data

(60) Provisional application No. 62/542,051, filed on Aug. 7, 2017.

(51) Int. Cl.
*A61B 1/307* (2006.01)
*A61B 1/00* (2006.01)

(52) U.S. Cl.
CPC ...... *A61B 1/307* (2013.01); *A61M 2025/1079* (2013.01); *A61M 2210/166* (2013.01)

(58) Field of Classification Search
CPC ....... A61B 2017/0496; A61F 2002/009; A61F 2250/0026; A61F 2250/0051; A61F 2250/0056; A61F 2250/0068; A61F 2/0077; A61F 2/1601
See application file for complete search history.

(56) References Cited

U.S. PATENT DOCUMENTS

| | | | |
|---|---|---|---|
| 4,832,688 A | | 5/1989 | Sagae et al. |
| 4,911,163 A | * | 3/1990 | Fina ................. A61B 17/22032 604/101.04 |
| 4,917,667 A | | 4/1990 | Jackson |
| 4,932,956 A | | 6/1990 | Reddy et al. |
| 4,932,958 A | | 6/1990 | Reddy et al. |
| 5,002,558 A | | 3/1991 | Klein et al. |
| 5,135,484 A | | 8/1992 | Wright |
| 5,163,905 A | | 11/1992 | Don Michael |
| 5,188,596 A | | 2/1993 | Condon et al. |
| 5,222,941 A | | 6/1993 | Don Michael |
| 5,314,409 A | | 5/1994 | Sarosiek et al. |
| 5,415,636 A | | 5/1995 | Forman |
| 5,588,965 A | | 12/1996 | Burton et al. |
| 5,713,861 A | | 2/1998 | Vanarthos |
| 5,718,678 A | | 2/1998 | Fleming, III |
| 5,797,869 A | | 8/1998 | Martin et al. |
| 5,947,977 A | | 9/1999 | Slepian et al. |
| 6,127,507 A | * | 10/2000 | Santerre .............. A61L 33/0076 428/423.1 |
| 6,494,879 B2 | | 12/2002 | Lennox et al. |
| 7,517,343 B2 | | 4/2009 | Tanghoj et al. |
| 2004/0116551 A1 | * | 6/2004 | Terry ..................... A01N 59/16 523/122 |
| 2005/0070938 A1 | * | 3/2005 | Copa ....................... A61B 17/11 606/153 |
| 2006/0173137 A1 | * | 8/2006 | McGlothlin ............... C08J 5/18 525/331.9 |
| 2006/0212022 A1 | * | 9/2006 | Gellman ........... A61M 25/0097 604/509 |
| 2013/0144272 A1 | | 6/2013 | Cutie |
| 2017/0100332 A1 | | 4/2017 | Tonkin et al. |
| 2017/0216543 A1 | * | 8/2017 | Magin ................... A61M 16/04 |

OTHER PUBLICATIONS

"Diagnostic Foley Catheters" Bard Medical, 2017, <www.bardmedical.com/products/urological-drainage/specialty-foley-catheters/diagnostic-foley-catheters>, Accessed Oct. 4, 2017 (3 Pages).

"Foley Catheter Selection Guide", Bard Medical, 2004, Retrieved from <www.bardmedical.com/products/urological-drainage/specialty-foley-catheters/diagnostic-foley-catheters> Oct. 4, 2017 (2 Pages).

"Hydrophilic Coating", brochure from Teleflex Medical OEM, 2017, Retrieved from <http://www.teleflexmedicaloem.com/diagnostic-and-interventional-catheters/hydrophilic-coatings/> Aug. 8, 2018 (4 Pages).

"Lubricious coatings suited for cardiovascular catheters", Medical Design Technology, Aug. 5, 2010, Retrieved from <https://www.mdtmag.com/product-release/2010/08/lubricious-coatings-suited-cardiovascular-catheters> Aug. 8, 2018 (2 Pages).

"Meeting the Needs of Urologists", Bard Medical, 2006, Retrieved from <www.bardmedical.com/products/urological-drainage/specialty-foley-catheters/diagnostic-foley-catheters> Oct. 4, 2017 (4 Pages).

"Special Foley Catheters, Sales Training Reference Guide", Bard Medical, 2004, Retrieved from <www.bardmedical.com/products/urological-drainage/specialty-foley-catheters/diagnostic-foley-catheters> Oct. 4, 2017 (66 Pages).

"Surface Modification Technology Platform, Endexo", Interface Biologics, 2018, Retrieved from <http://www.interfacebiologics.com/endexo.htm> Aug. 8, 2018 (5 Pages).

"The truth about medical devices & parylene coating", Diamond-MT, 2017, Retrieved from <https://blog.paryleneconformalcoating.com/medical-devices-and-parylene-coating-ubm-0?utm_source=GoogleAdwords&utm_medium=cpc&utm_campaign=MedicalDeciveCoatings&gclid=EAlaIQobChMIgpH_78yk3AIVmluzCh0p6wHWEAAYASAAEgKxD_D_BwE> Aug. 8, 2018 (2 Pages).

International Search Report and Written Opinion of the International Searching Authority dated Oct. 2, 2018 for International Application No. PCT/US2018/045402 (14 Pages).

Seegert, "Shark skin inspires antimicrobial surfaces", Med Device Online, Sep. 22, 2014, Retrieved from <https://www.meddeviceonline.com/doc/shark-skin-inspires-antimicrobial-surfaces-0001> Aug. 8, 2018 (2 Pages).

* cited by examiner

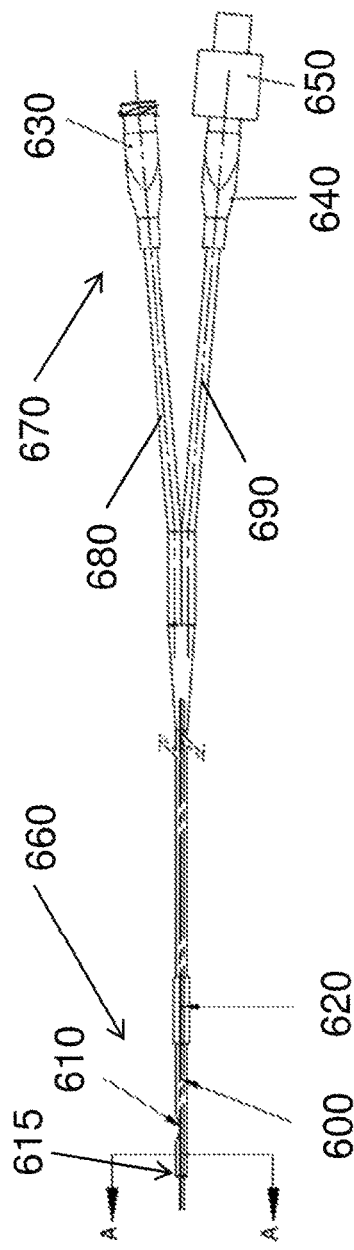
FIG. 6
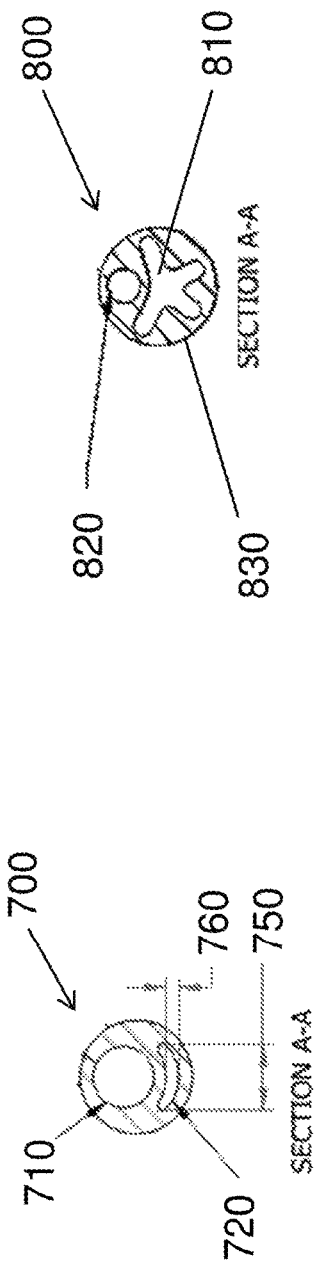
FIG. 7
FIG. 8

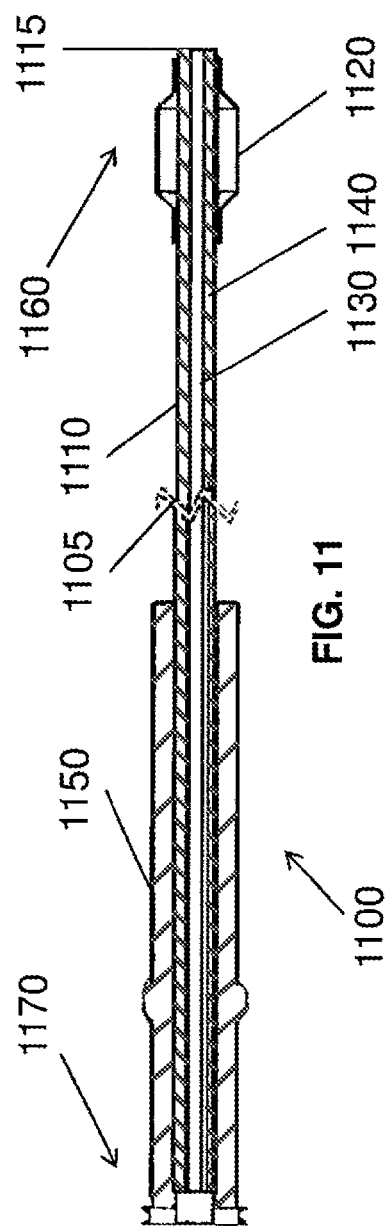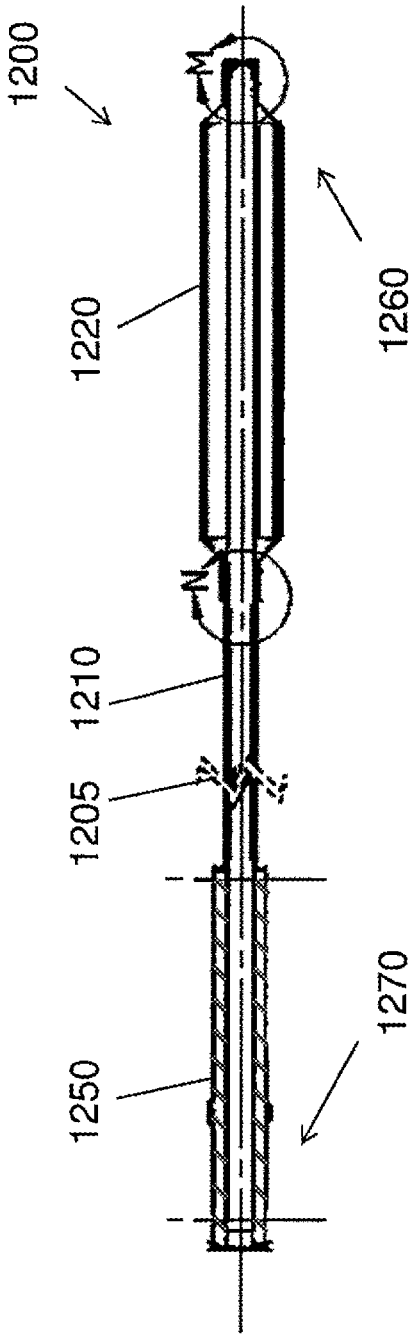

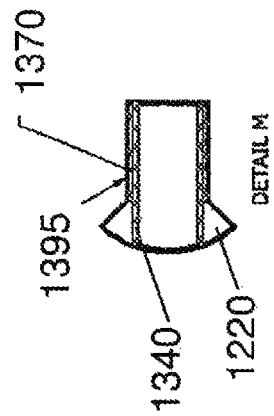
FIG. 14
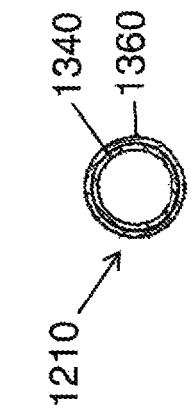
FIG. 17
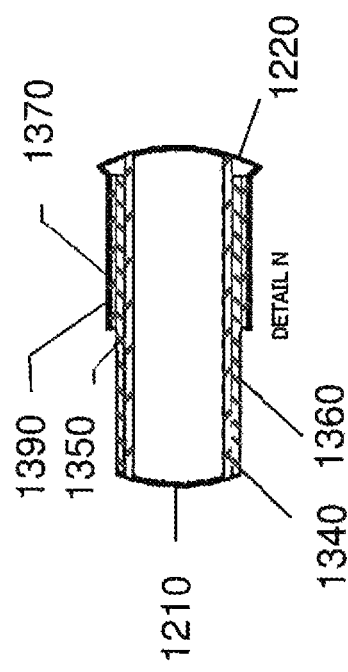
FIG. 13
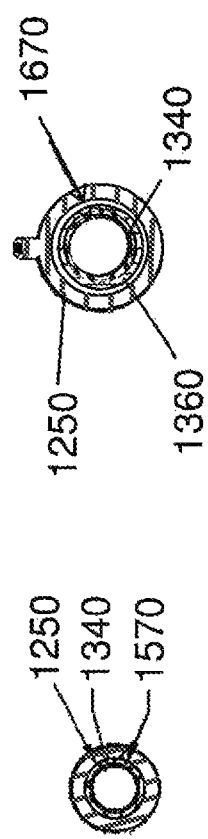
FIG. 16
FIG. 15

URETHRAL BALLOON DILATOR CATHETER

RELATED APPLICATIONS

This application is a continuation of U.S. Nonprovisional application Ser. No. 16/056,030, filed Aug. 6, 2018, which claims priority to and the benefit of U.S. Provisional Patent Application No. 62/542,051 filed Aug. 7, 2017, the entirety of each of which is incorporated herein by reference.

TECHNICAL FIELD

The invention relates to a medical device for dilating urethral strictures.

BACKGROUND

A urethral stricture is a narrowing of the urethra resulting in pain with urinating, bladder stone formation, urinary tract infection, and may lead to kidney damage. Urethral strictures may be post-procedural, instrumentation-related, or caused by injury, trauma, infection, radiation, and in many cases the cause is unable to be identified. Urethral strictures vary from short, soft narrowings of the urethra with minimal symptoms to panurethral, rigid strictures that require invasive reconstructive surgery or urinary diversion. Urethral strictures occur in a variety of places along the urethral lumen, largely depending on the cause of the stricture.

Treatment options include short-term balloon or rigid dilators, surgical excision of scar tissue with anastomosis, tissue grafting, or urinary diversion. Mechanical expansion is used in dilation of the strictures to soften the scar tissue and expand the urethral lumen diameter. Current practices perform expansion of the urethra to a fixed diameter or pressure over a short period of time. Other surgical specialties, such as plastic surgery, use techniques of tissue expansion over a longer duration (i.e. weeks to months). These techniques used over a longer time period increase tissue quantity and improve vascularity, resulting in healthier tissue with improved blood supply and less likely to reform scar. However, because the urethra is a necessary channel for draining urine from the bladder, the urethra cannot be completely obstructed for several weeks. Furthermore, if normal urethral tissue unrelated to the stricture is expanded for an extended period, damage to otherwise healthy urethral tissue may occur. If the tissue of the stricture is not treated, obstruction will remain.

SUMMARY

An apparatus in accordance with the invention provides prolonged dilation of urethral strictures in order to achieve stricture disruption, tissue expansion, and increased vascularity. The apparatus includes a dilator catheter that offers a high-pressure dilating force as well as a central lumen to drain urine from the bladder while the dilation balloon is in place. The apparatus also includes an adjustable sheath that positions the high-pressure dilating force coincident with the stricture once the catheter has been deployed within the urethra.

The invention may be embodied as a catheter with a localizing balloon, preferably a Foley-type balloon, and at least one high-pressure balloon for providing dilation force within the urethra. The localizing balloon positions the catheter at the bladder neck and reduces the likelihood of the catheter migrating off of the stricture and out of the patient, as can happen with temporary dilator balloons. Designs include fixed high-pressure dilator balloons with fixed sizes and positions along the catheter. For example, the high-pressure dilator balloons that may be approximately 5-8 cm distal to the localizing balloon, in order to bypass the prostatic urethra, and may be 10-15 cm in length to cover the bulbar and membranous urethra, where the vast majority of strictures occur. The dilator balloons are available in a variety of lengths and sizes to accommodate patient's unique physiology. The dilatory pressure of the dilator balloon may be adjusted based on characteristics of the stricture.

Urethral strictures occur in a variety of places along the urethral lumen. As such, the catheter of the invention is adjustable so that the locations of the one or more dilator balloons coincide with the stricture. The catheter may further include a plurality of dilator balloons located sequentially along the length of the catheter. Multiple lumens may pass longitudinally along the length of the catheter, connecting each dilator balloon with a corresponding port so that individual balloons may be inflated and deflated independently of one another. As such, within a series of dilator balloons, the individual balloon that overlaps most closely with the stricture can be selectively expanded while adjacent dilator balloons remain collapsed.

A medical device according to an aspect of the invention comprises a catheter and a sheath. The catheter comprises a first lumen, a proximal end, and a distal end. The proximal end comprises a first port. The distal end comprises an expandable occlusion member. The first lumen is in fluid communication with the first port and the expandable occlusion member. The catheter further comprises a second lumen configured to drain urine from the urinary bladder. The sheath is slidably disposed over the catheter between the first port and the expandable occlusion member. The sheath comprises an expandable member expandable independent of the expandable occlusion member.

In some embodiments, the device further comprises a second port in fluid communication with the expandable member. The sheath comprises a plurality of expandable members. Each expandable member of the plurality of expandable members is expandable independent of other expandable members. The expandable member is configured to withstand up to about 24 atm of force. The expandable member is configured to be expanded within a urethra of a patient. The expandable occlusion member is configured to be expanded within a urinary bladder of a patient. In certain embodiments, the expandable occlusion member is an occlusion balloon. The expandable member is a dilation balloon. In certain embodiments, one or more surfaces, or a portion of one or more surfaces, of catheter and/or sheath further includes a surface coating or surface modification.

In certain embodiments, the device further comprises a plurality of lumens disposed in the catheter, each lumen having a distal end and a proximal end, each lumen in fluid communication with a port at the proximal end and an expandable member of the plurality of expandable members at the distal end. For example, the catheter is a dual lumen catheter or a triple lumen catheter.

A medical device according to another aspect of the invention comprises a catheter. The catheter has a proximal end and a distal end. The catheter comprises a first lumen, a plurality of dilation lumens, a plurality of dilation ports, and a plurality of expandable members. The first lumen is in fluid communication with a first port at the proximal end and an expandable occlusion member at the distal end. Each dilation lumen of the plurality of dilation lumens has a distal portion and a proximal portion. Each dilation port of the plurality of dilation ports is located at the proximal portion of a dilation lumen from the plurality of dilation lumens. The plurality of expandable members is in fluid communication with the plurality of dilation lumens, each expandable member corresponding to a dilation lumen from the plurality of dilation lumens and disposed at the distal portion of the dilation lumen.

In some embodiments, the plurality of dilation ports is disposed on the catheter proximal to the first port. Each expandable member of the plurality of expandable members is expandable independent of the expandable occlusion member and is expandable independent of other expandable members. Each expandable member is configured to withstand up to 24 atm of force. Each expandable member is configured to be expanded within a urethra of a patient. The expandable occlusion member is configured to be expanded within a urinary bladder of a patient. The catheter further comprises a drainage lumen configured to drain urine from the urinary bladder. The expandable occlusion member is an occlusion balloon. Each expandable member is a dilation balloon. In some embodiments, each dilation port in the plurality of dilation ports is detachable from the catheter. In certain embodiments, one or more surfaces, or a portion of one or more surfaces, of the catheter further includes a surface coating or surface modification.

BRIEF DESCRIPTION OF THE DRAWINGS

FIG. 6 shows an embodiment of a catheter component of the device.

FIG. 7 shows a cross-sectional view of a catheter component according to an embodiment of the device.

FIG. 8 shows a cross-sectional view of a catheter component according to an embodiment of the device.

FIG. 11 shows a cutaway view of a longitudinal section of an inner catheter according to an embodiment.

FIG. 12 shows a cutaway view of a longitudinal section of an outer sheath according to an embodiment.

FIG. 13 shows an embodiment illustrating attachment of a dilation balloon from the circular section of FIG. 12 labeled N.

FIG. 14 shows an embodiment illustrating attachment of a dilation balloon from the circular section of FIG. 12 labeled M.

FIG. 15 shows a cross-sectional view of the port portion proximal to the dilation port of the outer sheath according to an embodiment shown in FIG. 12.

FIG. 16 shows a cross-sectional view of the port portion distal to the dilation port of the outer sheath according to an embodiment shown in FIG. 12.

FIG. 17 shows a cross-sectional view of the hollow tubing of the outer sheath according to an embodiment shown in FIG. 12.

DESCRIPTION

The invention relates to a medical device for dilating urethral strictures for prolonged periods of time. Positioning of the device within the urethra will be done following cystoscopic and/or radiographic evaluation of the urethral stricture. As part of the installation of the device within the urinary system of a male human patient, or any other mammal with the same or a similar urinary system, a cystoscope is advanced to the distal end of the urethral stricture. An occlusion balloon catheter, such as the occlusion balloon catheter sold under the trademark FOGARTY by Edwards Lifesciences Corporation (Irvine, Calif.), with distance markings on the catheter is advanced through the stricture into the urinary bladder. Once in the bladder, the balloon is expanded and pulled snug to the bladder neck to approximate the distance from the bladder neck to the distal end of the urethral stricture via the catheter markings. Optionally, the balloon is partially deflated to pull the device further proximal, which allows a user, such as a healthcare professional, to estimate the proximal and distal ends of the stricture. This is similar to the urethral length measuring method described in U.S. Pat. No. 5,002,558.

Once positioned, the catheter will be left in place in the urethra of the human patient for a prolonged period of time, such as six weeks. A healthcare professional may monitor the patient and extend or reduce the period of time accordingly. The healthcare professional will monitor the patient periodically after placement of the device, such as every three days. The healthcare professional will adjust the device after placement to gradually add volume to the dilator balloon, thereby causing progressive mechanical dilation. Preferably, the pressure of the dilator balloon is increased up to 24 atm. A healthcare profession may confirm positioning of the localizing balloon, positioning of the dilator balloons, and drainage of the bladder. The device may be removed after a prescribed time period.

Figure 1:
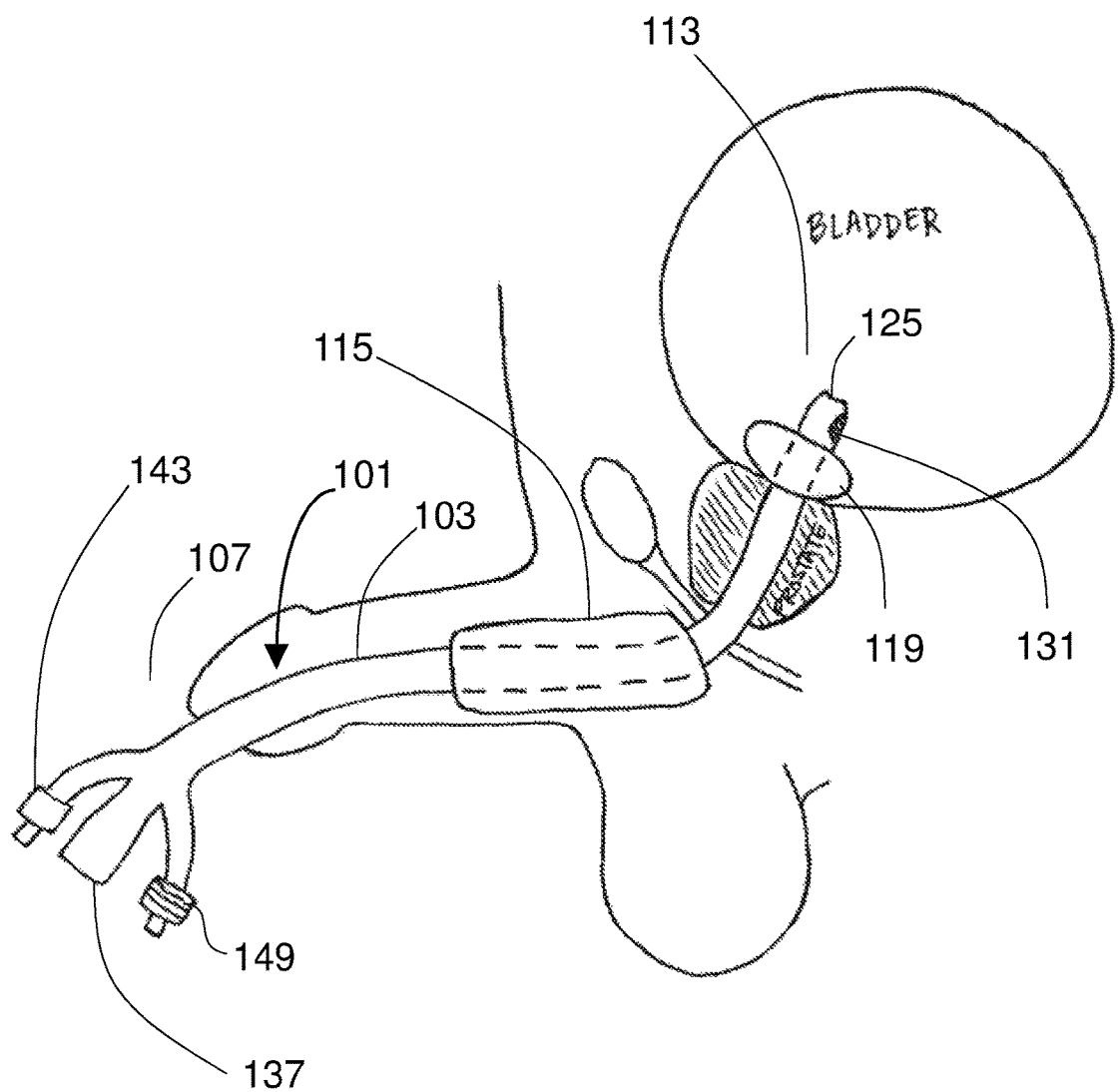
FIG. 1 illustrates a device in accordance with the invention and deployed within a body of a male human patient.

FIG. 1 illustrates an embodiment of a device according to the invention. The device is shown in a male human patient. The apparatus, or device, comprises a catheter 103. The catheter 103 has a diameter to accommodate pre-dilation stricture diameters. Catheter size may be measured according to the French scale system. For example, the diameter may be between 10 and 14 French. At 10 French, the circumference of the catheter is 10.47 mm, and the outer diameter of the catheter is 3.333 mm. At 14 French, the circumference of the catheter is 14.66 mm, and the outer diameter of the catheter is 4.667 mm.

The catheter 103 may comprise any suitable material. Preferably, the catheter 103 is made of a material that allows ease of insertion of the catheter into (and removal from) the urethra. The catheter 103 should be rigid enough that it may be pushed through strictures within the urethra. For example, the catheter may be formed from silicon rubber, latex, nylon, polyurethane, polyethylene terephthalate (PET), thermoplastic elastomers, and related materials.

The catheter 103 includes a proximal portion 107 and a distal portion 113. The distal portion 113 includes a localizing balloon 119, such as a Foley-type inflation/deflation balloon sold by C. R. Bard, Inc. (Covington, Ga.), and a dilator balloon 115 proximal to the localizing balloon 119. The distal portion 113 further includes at least one hole 131 for drainage of urine from the bladder of the patient. The device may further comprise a loading hole 125 to facilitate the loading and advancement of the catheter 103 into the patient's body over a wire.

For example, the guidewire would be placed cystoscopically to ensure passage of wire into the urinary bladder. The cystoscope would be removed leaving the wire in place traversing the urethral stricture. The device could then be advanced over the wire by inserting the exterior end of the wire into loading hole 125 at the distal tip that would pass through the urine drainage lumen and out of proximal hole 137. Once the catheter is advanced into the urinary bladder, the guidewire could be removed and urine would drain through this lumen.

In an embodiment, the proximal portion 107 of the catheter 103 includes a urine drainage port 137, a localizing balloon port 143, and a dilator balloon port 149. The respective ports may be formed of any suitable material. In an example, the port is formed of a pliable latex or rubber. The ports are configured to accept or connect to any suitable attachment.

The urine drainage port 137 may be configured to receive catheter-tip syringes and urine drainage bag attachments. The localizing balloon port 143 may be an injection/aspiration valve with a female connector for a syringe. In an embodiment, the localizing balloon port or occlusion balloon port is an injection/aspiration valve with a female connector for a 10 cc syringe male adaptor with no attachment mechanism.

The dilator balloon port 149 may include an injection/aspiration valve with a Luer-Lock screw attachment or similar fitting to maintain dilation pressure. The volume and pressure of the dilator balloon 115 may be adjusted by a hand or a manometer pump at the dilator port 149 to precisely measure the dilation pressure. The dilator balloon 115 preferably is constructed of a material made to withstand up to approximately 24 atm of force. The size and shape of the dilator balloon 115 can have any number of valves such that it accommodates the patient's urethral structure.

Figure 2:
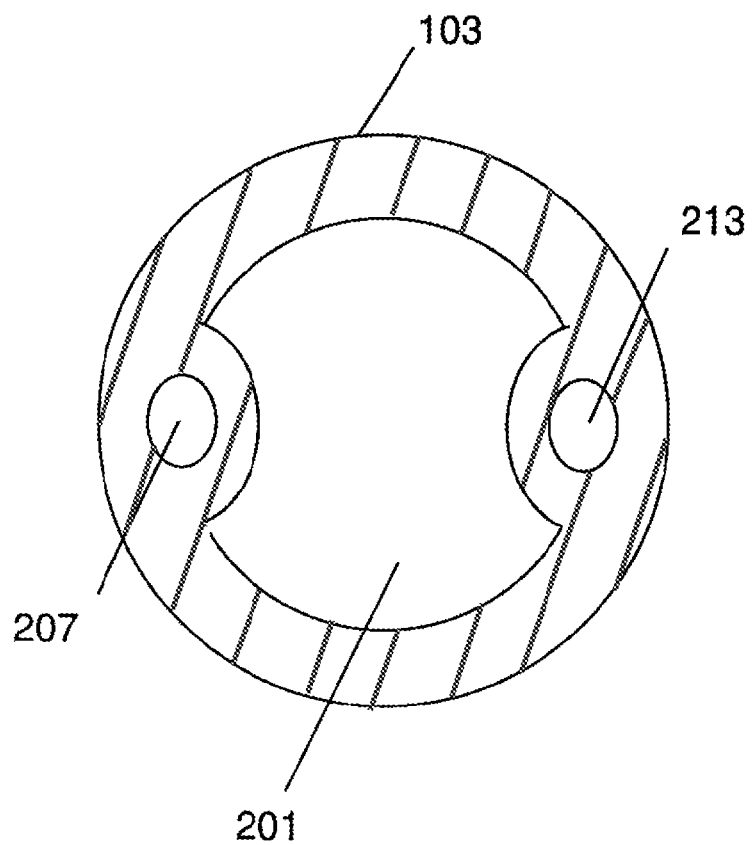
FIG. 2 shows a cross-sectional view of an embodiment of the device.

FIG. 2 shows a cross-sectional view of the catheter 103 described in FIG. 1. The catheter 103 includes a central lumen 201 for drainage of urine from the urinary bladder. The catheter 103 further includes a localizing balloon lumen 207 and a dilator balloon lumen 213 for inflation/deflation of the localizing balloon 119 and dilator balloon 115, respectively. The lumens run longitudinally along the length of the catheter 103, connecting the distally located balloons to respective ports on the proximal end. It should be understood that while the depicted embodiment illustrates three lumens, the actual number of lumens will depend on the number of dilator balloons 115 disposed on the device. Each balloon employed by the device may correspond with a respective lumen such that individual balloons may be inflated/deflated independently of one another.

Figure 3:
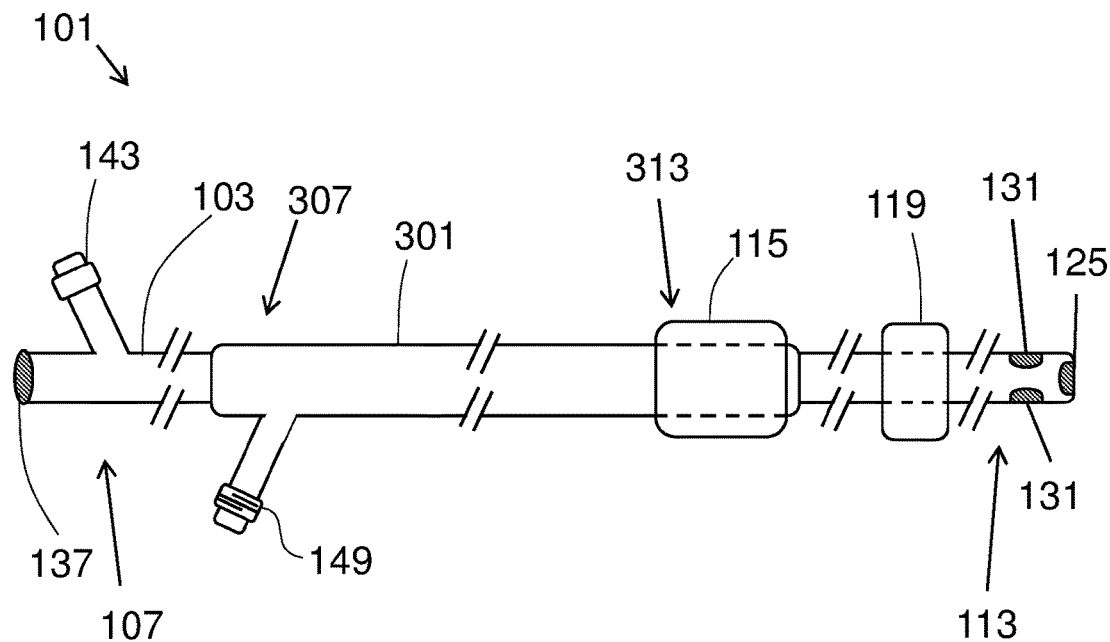
FIG. 3 shows an embodiment of a device with a sliding outer sheath.

FIG. 3 illustrates a catheter with a sliding outer sheath 301 according to another embodiment of the invention. The outer sheath 301 includes a proximal end 307 and a distal end 313. The outer sheath 301 further comprises at least one dilator balloon 115 located near the distal end 313 along with at least one dilator port 149 located on the proximal end 307. The dilator, or inflation, ports may have any suitable attachment configuration, such as a Luer-Lock attachment configuration. The dilator port may be coupled with a fluid source to dilate, or inflate, the dilator balloon.

The distal portion 113 of the catheter 103 includes a localizing balloon 119 and at least one hole 131 for drainage of urine from the bladder, as well as a loading hole 125 for installing the catheter 103 in the body over a wire as described above. The proximal portion 107 of the catheter 103 includes a urine drainage port 137 and a localizing balloon port 143. The outer sheath 301 is configured to slide along the catheter 103 between the localizing balloon 119 and the localizing balloon port 143 for the purpose of positioning the one or more dilator balloons 115 within the urethra at the specific site of the stricture after the catheter 103 has been installed. Preferably, the one or more high-pressure dilator balloons 115 will be available in a range of sizes and lengths and constructed of a material capable of withstanding up to approximately 24 atm of pressure. The one or more dilator balloon ports 149 will preferably comprise an injection/aspiration valve with a Luer-Lock adaptor, or an adaptor of a similar style. The outer sheath 301 length will be less than the catheter 103, but long enough that the proximal end 307 of the outer sheath 301 may extend from the patient's body while the dilator balloon 115 is positioned coincident with the stricture.

The outer sheath 301 may slide from an initial insertion site to an area that overlaps with the stricture. The distance that the outer sheath 301 is moved may depend on measurements taken prior to the insertion of the catheter 103 into the urethra. By providing a catheter 103 with a sliding outer sheath 301 the dilator balloon 115 may be positioned within the urethra precisely at the site of the stricture once the device is inserted into the body. The device may include radiographic markers to assist in precise localization of the dilator balloon.

Figure 4:
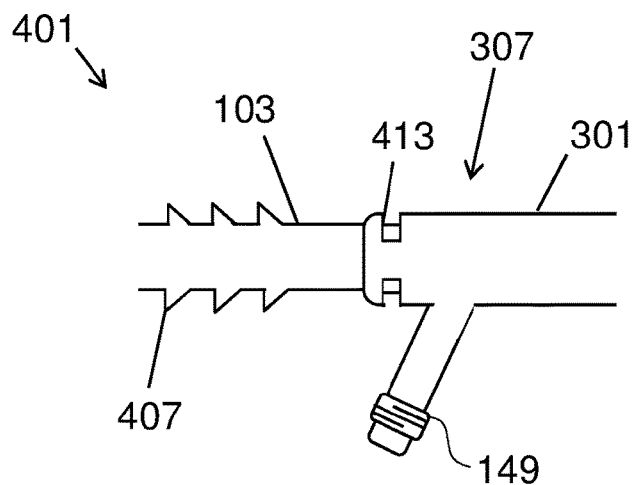
FIG. 4 illustrates an arrangement for fixing a position of the outer sheath over an inner catheter of the device.

As shown in FIG. 4, there can be an arrangement that allows the outer sheath 301 to be fixed to a position along the catheter 103. Once the device has been inserted into the body, and the outer sheath 301 is slid into a desired position, a connector 401 may be engaged to releasably fix the outer sheath 301 to the catheter 103 and restrict any further movement between the outer sheath 301 and the inner catheter 103. The exemplary connector 401 of FIG. 4 involves the catheter 103 having a series of teeth, tabs, ribs, or similar projections 407 along its surface, and these projections 407 are configured to be received by recesses, holes, grooves or similar indentions 413 located on at the proximal end 307 of the outer sheath 301. Once two or more of the projections 407 are received by corresponding two or more of the indentations 413, relative movement between the outer sheath 301 and the inner catheter 103 (both longitudinal and rotational) is restricted until enough force is applied to the outer sheath 301 and/or the inner catheter 103 to move the retained projection(s) 407 out of the indentation(s) 413. Other means of affixing the outer sheath to the inner catheter to prevent displacement may be employed. For example, a Tuohy Borst adapter may be employed.

Figure 5:
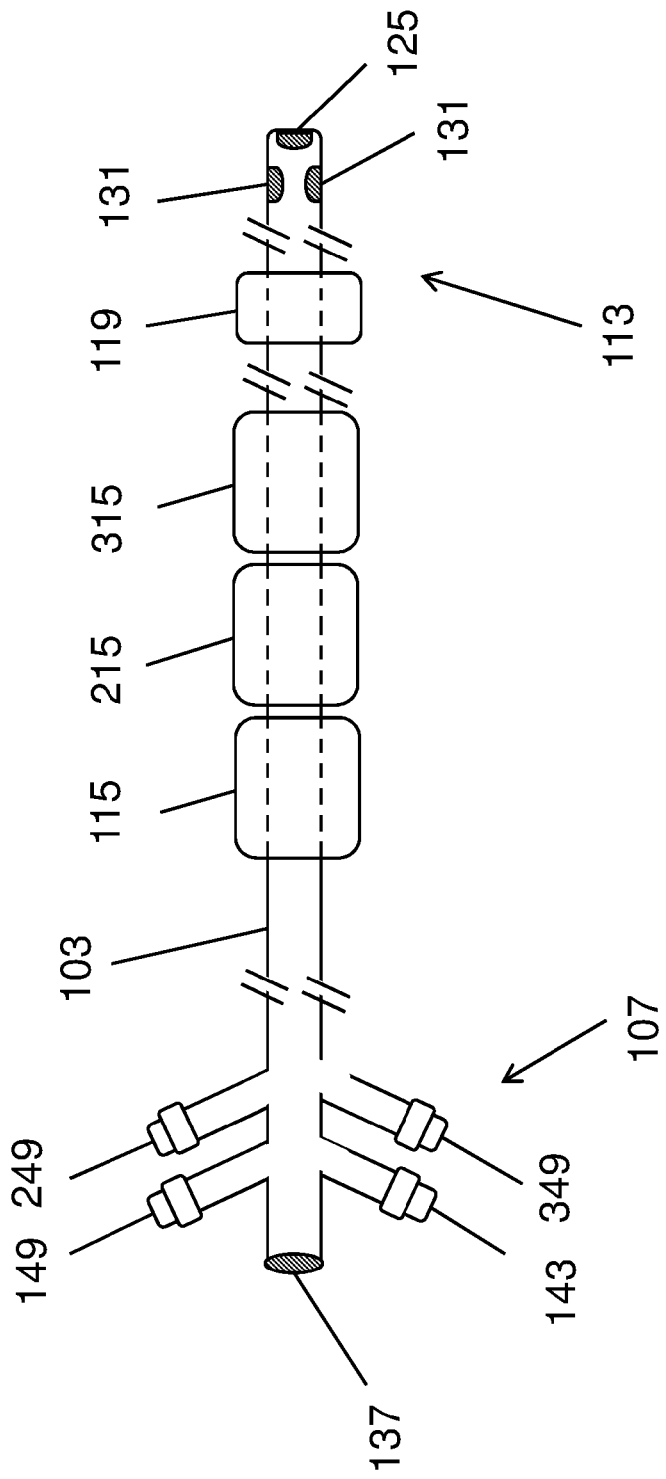
FIG. 5 shows an embodiment of a device with a plurality of dilating balloons.

FIG. 5 shows an embodiment where the catheter 103 includes a plurality of dilator balloons 115, 215, 315 located sequentially along the length of the distal portion 113 of the catheter 103. Although three dilator balloons 115, 215, 315 are depicted, the device may employ any number of balloons. Preferably, multiple lumens will extend longitudinally along the length of the catheter 103 so that each balloon will be connected to a respective port for inflation/deflation and maintaining fluid within the corresponding balloon.

As previously described, the localizing balloon 119 may be located on the distal portion 113 of the catheter 103 and connected to a localizing balloon port 143 attached at the proximal portion of the catheter 103. The localizing balloon port 143 may be an injection/aspiration valve with a female connector for a syringe.

The dilating balloons 115, 215, 315 will preferably be high-pressure balloons formed of a material capable of achieving up to 24 atm. The corresponding dilator balloon ports 149, 249, 349 may include an injection/aspiration valve with a Leur-Lock screw attachment, or similar fittings, for attaching a balloon catheter pump. While three dilator balloon ports 149, 249, 349 are depicted, the actual number of dilator balloon ports 149 can be any number, but should be consistent with the number of dilator balloons 115, 215, 315. Providing multiple dilator balloons allows for expansion of a longer segment of the urethra, should the urethral strictures encompass a longer segment of the urethra.

FIG. 6 shows an embodiment of the inner catheter component of the device. The catheter 600 is a long tubular catheter, e.g. 70 cm in length, with more than one lumen arranged therein, and the breakage points in the figure depict the length of the catheter. The catheter 600 has a distal end 660 and a proximal end 670. A guidewire hole 615 is located at the distal end 660 of the catheter 600 which is the distal opening of urine drainage lumen 680. A guidewire is threaded through the guidewire hole 615 through lumen 680 and out the proximal port 630 to ensure passage of the catheter across the urethral stricture into the bladder. An additional urine drainage hole, or urine flow skive, 610 is located proximal to the guidewire hole 615 at the distal end 660 of the catheter 600. The urine drainage hole 610 and guidewire hole 615 are in fluid communication with the urine drainage lumen 680 and the urine drainage port 630.

Proximal to the urine drainage hole 610 is the occlusion balloon 620. For example, the occlusion balloon is a chronoprene balloon. The occlusion balloon 620 is in fluid communication with the occlusion balloon inflation lumen 690 and the occlusion balloon inflation port 640. An occlusion balloon inflation check valve 650 is located at the proximal end of the occlusion balloon inflation port 640. The ports 630 and 640 may have any suitable attachment connections. For example, the ports may have a Luer-Lock attachment or other valve components on port 630 to maintain dilation pressure and decrease size of the external portion of the device.

FIG. 7 shows a cross-sectional view of a catheter 700 according to an embodiment of the device. The urine flow/guidewire lumen 710 is shown as a circular cross-section, while the occlusion balloon inflation lumen 720 is shown as a crescent cross-section. The catheter may be any suitable size, and the size of the catheter may vary by patient. In an example, the catheter 700 has a 0.010 inch wall thickness, which may be in triplicate. In an example, the outer diameter 730 of the catheter is 0.085 inch, the urine drainage lumen 710 has a diameter of 0.046 inch, and the occlusion balloon inflation lumen 720 has a cross-sectional area of 0.00094 square inch, a width of 0.049 inch, and a height of 0.010 inch. In an example, outer diameter 730 of the catheter is 0.095 inch, the urine drainage lumen 710 has a diameter of 0.052 inch, and the occlusion balloon inflation lumen 720 has a cross-sectional area of 0.0016 square inch, a width of 0.065 inch, and a height of 0.010 inch.

FIG. 8 shows a cross-sectional view of a catheter 800 according to an embodiment of the device. The lumen configuration shown in the cross-sectional view resembles a gingerbread man and maximizes the cross sectional area of the urine drainage/guidewire lumen 810 for urine flow while minimizing the outer diameter 830. This provides improved tensile and circumferential strength for the catheter 800. The size of the catheter may be any suitable size, and the size of the catheter may vary by patient. In an example, the diameter of the occlusion balloon lumen 820 is at least about 0.031 inch. As an example, the outer diameter 830 of the catheter 800 is 0.110-0.120 inch, is 0.113-0.117 inch, and preferably is 0.115 inch. The urine drainage lumen 810 corresponds to the "body" portion of the gingerbread man, while the "head" of the gingerbread man corresponds to the occlusion balloon lumen 820 for connecting the positioning balloon in the bladder.

Figure 9:
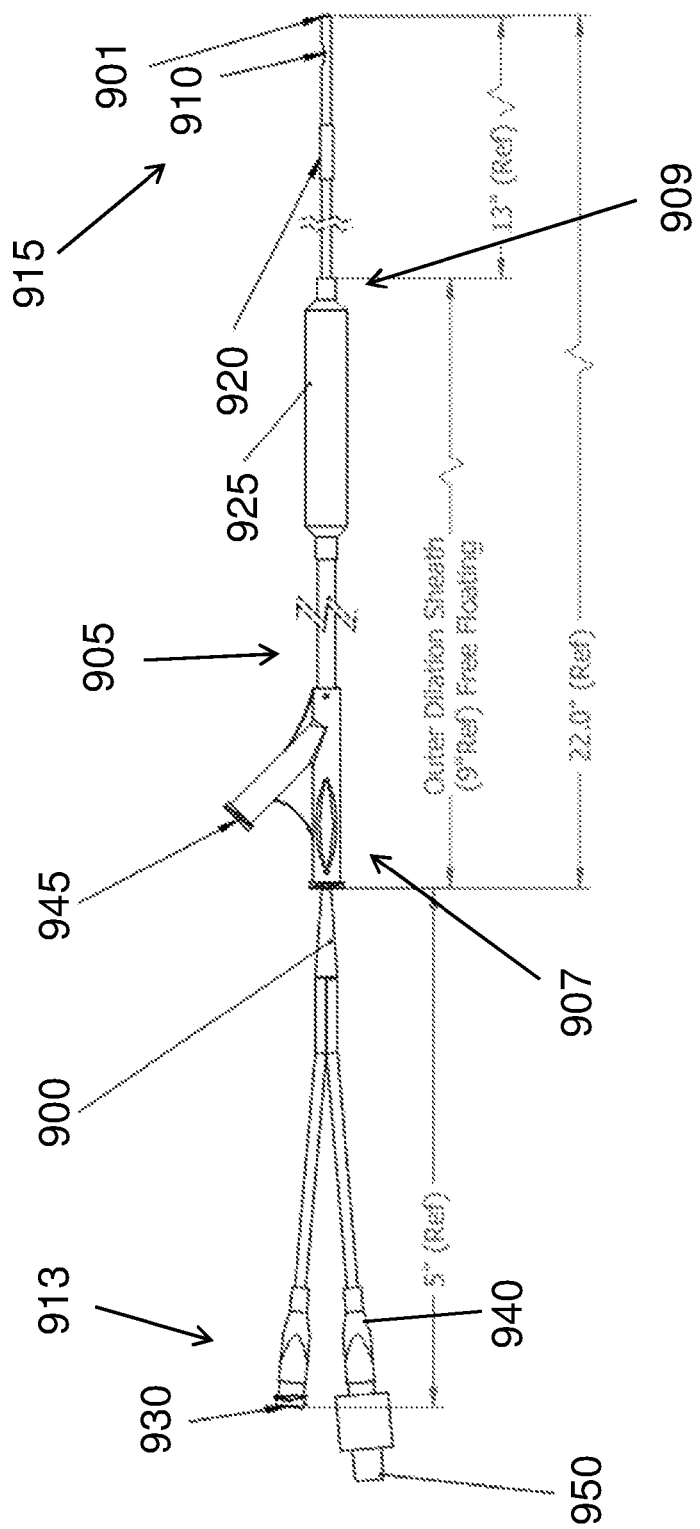
FIG. 9 shows an embodiment of the device with a catheter component disposed in a sheath component.

FIG. 9 shows an embodiment of the device with an outer sheath 905 over an inner catheter 900. The catheter 900 has a proximal end 913 and a distal end 915 with an open-ended tip 901. The outer sheath 905 has a distal end 909 and a proximal end 907. The outer sheath has a dilator balloon 925 at the distal end 909 and a dilation port 945 at the proximal end 907. In certain embodiments, the dilation port 945 is removable from the outer sheath 905, which minimizes bulk of the device.

The outer dilation sheath 905 may be free floating over the inner catheter 900 and may be any suitable length. For example, the outer dilation sheath 905 may be 9 inches in length. The one or more dilator balloons 925 may be any suitable length. For example, a dilator balloon 925 may be 3-7 cm in length. In an example, the dilator balloon 925 may be 5 cm in length.

In an example, the device is 27 inches in length from the ports 930 and 940 to the open-ended tip 901. The catheter port connections 930 and 940 are 5 inches in length. The portion of the device excluding the 5 inches of the catheter port connections is 22 inches in length, with 9 inches allocated to the outer dilation sheath 905 and 13 inches allocated to the distal end 915 of the catheter, which comprises the open-ended tip 901, the urine drainage hole 910, and the occlusion balloon 920.

Figure 10:
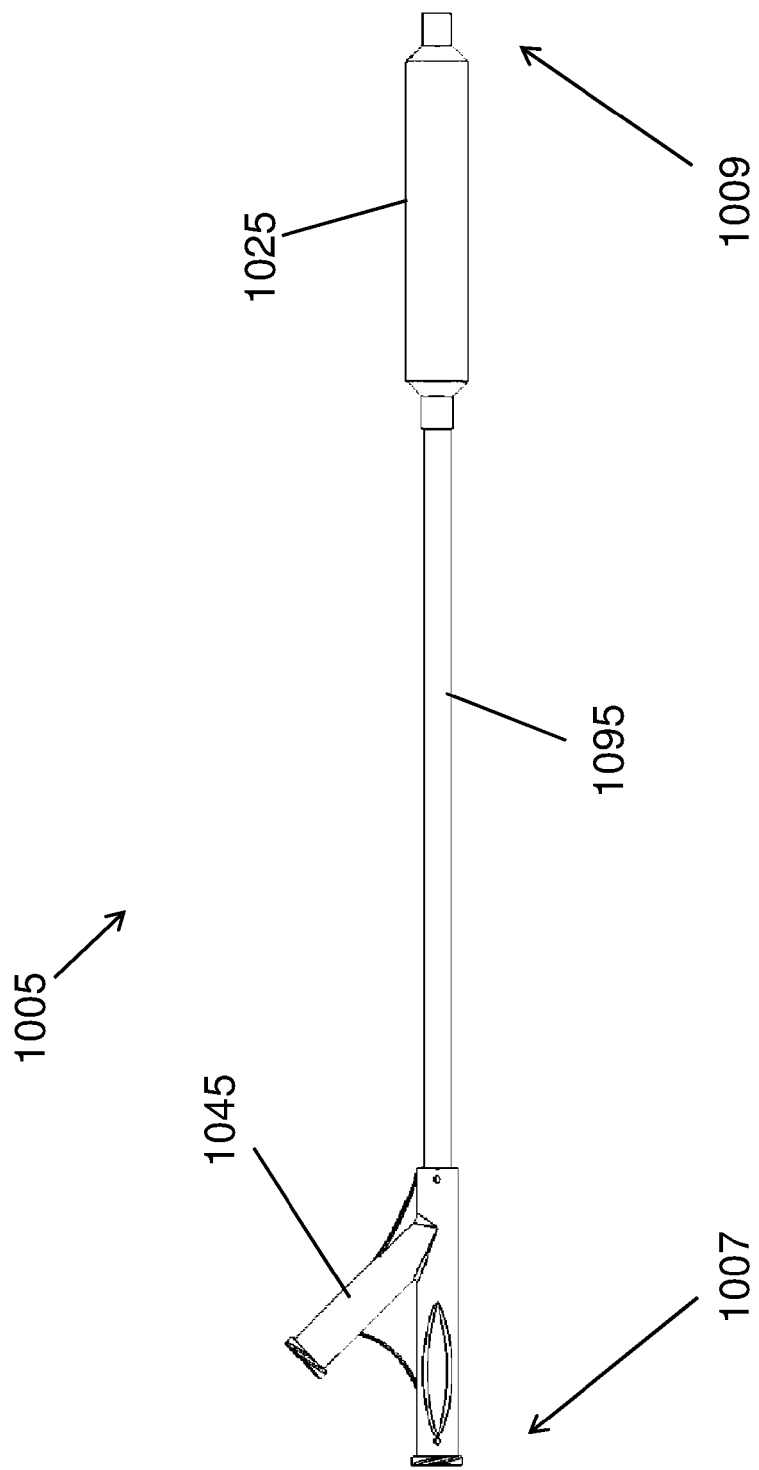
FIG. 10 shows an embodiment of a sheath component.

FIG. 10 shows an embodiment of the sheath component, or outer sheath, 1005 without an inner catheter disposed within the sheath 1005. The outer sheath 1005 comprises a central sheath lumen 1095 configured to be disposed on the catheter component, or inner catheter. The sheath 1005 may be any suitable length. The length of the outer sheath 1005 may vary depending on the length of tubing in the inner catheter. For example, the outer sheath may be 9 inches in length from a proximal end 1007 to a distal end 1009.

The outer sheath 1005 may comprise one or more dilation balloons 1025 at the distal end 1009. The one or more dilation balloons 1025 may be any suitable length. The number of dilation balloons and length of the dilation balloons may vary according to the length of the urethral stricture in a patient. For example, a dilation balloon 1025 may be 5 cm in length.

The outer sheath 1005 further comprises a dilation port 1045 at the proximal end 1007. The dilation balloon 1025 is in fluid connection with the dilation port 1045. The dilation port 1045 and dilation balloon 1025 may have any suitable connection to the central sheath lumen 1095 of the outer sheath 1005. For example, the dilation port 1045 and dilation balloon may be glued to the central sheath 1095. In certain embodiments, the dilation port 1045 is removable, or detachable, from the outer sheath 1005. Removing the dilation port minimizes bulk of the device.

FIG. 11 shows a cutaway view of a longitudinal section of an inner catheter 1100 according to an embodiment. The dashed zig-zag line 1105 designates a break in the tubing 1110 of the catheter 1100, as the inner catheter 1100 may be any suitable length. The inner catheter 1100 has a proximal portion 1170 and a distal portion 1160. An open-ended tip 1115 is located at the distal portion 1160. Proximal to the open-ended tip 1115 is the occlusion balloon 1120. The tubing 1100 of the inner catheter 1100 may comprise a plurality of lumens, such as a urinary drainage lumen 1130 and an occlusion balloon dilation lumen 1140. At the proximal portion 1170 of the inner catheter 1100 is the port section 1150. The port section 1150 may have a port for each lumen disposed in the inner catheter 1100.

FIG. 12 shows a cutaway view of a longitudinal section of an outer sheath 1200 according to an embodiment. The dashed zig-zag line 1205 designates a break in the hollow tubing 1210 of the outer sheath 1200, as the outer sheath 1200 may be any suitable length and is configured to be disposed around an inner catheter. The outer sheath 1200 has a proximal end 1270 and a distal end 1260. A dilation balloon 1220 is located at the distal end 1260. A port portion 1250 is located at the proximal end 1270, the port portion 1250 having a dilation port for each dilation balloon 1220 of the outer sheath 1200.

FIG. 13 shows an embodiment illustrating attachment of a dilation balloon from the circular section of FIG. 12 labeled N. The dilation balloon 1220 may be disposed on the hollow tubing 1210 by any suitable means. For example, the end 1390 of the dilation balloon 1220 may be glued to the hollow tubing 1210 of the outer sheath, as shown by glue gap 1370. A balloon inflation gap 1350 is shown between an inner tubing layer 1340 and an outer tubing layer 1360 of the hollow tubing 1210. The outer tubing layer 1360 does not continue through the length of the dilation balloon in order to allow fluid communication to the dilation balloon. The inner tubing layer 1340 continues through the length of the dilation balloon. The balloon inflation gap 1350 is in fluid communication in with the dilation balloon 1220 and the dilation port and fluid travels through the balloon inflation gap 1350 to inflate the dilation balloon 1220.

FIG. 14 illustrates attachment of a dilation balloon from the circular section of FIG. 12 labeled M. The end 1395 of the dilation balloon 1220 shown in the circular section of FIG. 12 labeled M may be sealed by any suitable means. For example, the end 1395 may be glued to the inner tubing layer 1340 of the outer sheath, as shown by the glue gap 1370.

FIG. 15 shows a cross-sectional view of the port portion 1250 proximal to the dilation port of the outer sheath according to an embodiment shown in FIG. 12. The inner tubing layer 1340 of the hollow tubing 1210 is disposed within the port portion 1250. The port portion may be disposed on the inner tubing layer of the hollow tubing by any suitable means at the proximal part of the outer sheath. In an example, the port portion is glued to the inner tubing layer, as shown by the glue gap 1570.

FIG. 16 shows a cross-sectional view of the port portion 1250 distal to the dilation port of the outer sheath according to an embodiment shown in FIG. 12. The inner tubing layer 1340 of the hollow tubing 1210 is disposed within the outer tubing layer 1360 of the hollow tubing 1210. The outer tubing layer 1360 is disposed within the port portion. The outer tubing layer 1360 may be glued to the port portion, as shown by the distal glue gap 1670. The port portion may be any suitable size. In an example, the port portion has an inner diameter of 0.185 inches.

FIG. 17 shows a cross-sectional view of the hollow tubing 1210 of the outer sheath according to an embodiment shown in FIG. 12. The hollow tubing 1210 comprises the inner tubing layer 1340 disposed within the outer tubing layer 1360 to provide a balloon inflation gap 1350 between the inner tubing layer 1340 and the outer tubing layer 1360. The inner and outer tubing layers may be any suitable size. In an example, an inner diameter of the inner tubing layer is 0.120±0.002 centimeters, an outer diameter of the inner tubing layer is 0.140±0.002 centimeters, an inner diameter of the outer tubing layer is 0.145±0.002 centimeters, and an outer diameter of the outer tubing layer is 0.165±0.002 centimeters.

In certain embodiments, one or more surfaces of the device comprise a surface coating or surface modification. The surfaces of the device comprise any suitable surface, such as the inner and outer surfaces of the catheter and/or sheath. In an example, the catheter and sheath comprise a surface coating or surface modification. Surface coatings and surface modifications are used to affect adhesion, asepsis, biocompatibility, chemical inertness, degradation, hydrophilicity, lubricity, sterility, surface energy, susceptibility to corrosion, lithogenicity, and thrombogenicity in order to maximize performance of the device. Embodiments of the invention may comprise surface coatings and/or surface modifications that achieve any, or all, of the aforementioned features.

A surface coating comprises adding one or more coatings to one or more surfaces, or one or more portions of one or more surfaces, of the device. Surface coatings may provide decreased encrustation, particularly for an indwelling catheter, and may comprise anti-fibrotic materials, which help to prevent stricture recurrence. In an example, surface coatings provide a lubricious surface of the device, which allows for ease of insertion and removal, and thereby less pain and resistance in the patient during the insertion and removal process. In another example, surface coatings provide an anti-microbial surface on the device, reducing microbial accumulation on the device. Surface coatings may prevent encrustation and build-up of biological material on the device.

For example, components of the device may comprise a coating on one or more surfaces of the device. The surface coating may be selected from an antibiotic coating, a parylene conformal coating, a hydrophilic coating, and a lubricious coating (such as a coating sold under the trademark e.g., BAYMEDIX CL 100 by Bayer MaterialScience LLC). In another example, components of the device may be coated with or incorporate a noble metal, such as incorporation with silver salts, ions, and complexes and incorporation or coating with nanostructured silver, gold, cooper, and palladium.

A surface modification comprises modifying one or more surfaces, or one or more portions of one or more surfaces, of the device. Surface modifications may inhibit adherence of biological material on the device by providing a texture that is undesirable for adherence, such as a microscopic, pointy surface. In an example, components of the device comprise surface modifications, such as a plasma modification of the device or a texture that discourages biofilm formation (e.g., such as described in U.S. Publication No. 2017/0100332 and U.S. Publication No. 2017/0216543 by Sharklet Technologies, Inc.).

In an example, surface modifying molecules are added and compounded prior to the normal manufacturing process for the device. By adding the surface modifying molecules prior to the normal manufacturing process, a change in the existing manufacturing process, such as extrusion, injection molding, and solution spinning, is not required. The surface modifying molecules may be compatible with a wide range of base materials used in the manufacturing process, such as base polymers, i.e., polypropylene, polysulfone, polyurethane, polyvinylchloride, and silicone. In an example, surface modifying molecules such as low molecular weight additives sold under the trademark ENDEXO by Interface Biologics Inc. (Toronto, Ontario) are added to a base polymer and compounded before manufacturing.

The foregoing description is illustrative of certain embodiments according to the invention, and it is not intended to be limiting in any way on the invention. Any and all references and citations to other documents, such as patents, patent applications, patent publications, journals, books, papers, and web contents, which have been made throughout this disclosure, are hereby incorporated herein by reference in their entirety for all purposes. Also, aspects of different disclosed device embodiments should be considered to be possible aspects of any of the disclosed embodiments, whether expressly stated as such or not.

What is claimed is:

1. A medical device for use in dilating a stricture in a urethra of a patient, comprising:
    a catheter comprising a first lumen, a second lumen, a proximal portion, and a distal portion, the proximal portion of the catheter comprising a first port and a second port, the distal portion of the catheter comprising an expandable occlusion member and at least two urine drainage ports, the first lumen in fluid communication with the first port and the expandable occlusion member, the second lumen in fluid communication with the second port and the at least two urine drainage ports; and
    an outer sheath slidably disposed over the catheter between the first port and the expandable occlusion member, the outer sheath comprising an expandable dilation member that is slidable over the catheter along with the outer sheath and that is expandable independent of the expandable occlusion member, the outer sheath comprising a dilation lumen, a proximal portion, and a distal portion, the proximal portion of the outer sheath comprising a dilation port, the distal portion of the outer sheath comprising the expandable dilation member, the dilation lumen in fluid communication with the dilation port and the expandable dilation member;
    the proximal portion of the outer sheath including an outer surface, and an end of the dilation port is attachable to and detachable from the outer surface of the proximal portion of the outer sheath;
    the outer sheath and the catheter configured to be releasably fixed to each other to restrict relative movement between each other, once the outer sheath is slid over the catheter to position the expandable dilation member at the stricture in the urethra of the patient;
    wherein the catheter includes projections configured to be received by openings or indentations in the proximal portion of the outer sheath to thereby releasably fix the catheter to the outer sheath to restrict relative movement between each other, once the outer sheath is slid over the catheter to position the expandable dilation member at the stricture in the urethra of the patient; and
    the expandable dilation member configured to expand within the urethra and apply a dilation force to the stricture from within the urethra.

2. The device of claim 1, wherein the expandable dilation member is configured to withstand up to about 24 atm of force.

3. The device of claim 1, wherein the expandable occlusion member is configured to be expanded within a urinary bladder of the patient.

4. The device of claim 3, wherein the second lumen is configured to drain urine from the urinary bladder to the second port.

5. The device of claim 1, wherein the expandable occlusion member is an occlusion balloon.

6. The device of claim 1, wherein the expandable dilation member is a dilation balloon.

7. The device of claim 1, wherein the catheter is a dual lumen catheter.

8. The device of claim 1, wherein at least a portion of a surface of at least one of the catheter and the outer sheath includes at least one surface coating.

9. The device of claim 8, wherein the surface is an inner surface of at least one of the catheter and the outer sheath.

10. The device of claim 8, wherein the surface is the outer surface of the outer sheath or an outer surface of the catheter.

11. The device of claim 8, wherein the at least one surface coating is used to affect one or more of adhesion, asepsis, biocompatibility, chemical inertness, degradation, hydrophilicity, lubricity, sterility, surface energy, susceptibility to corrosion, lithogenicity, and thrombogenicity.

12. The device of claim 8, wherein the at least one surface coating provides decreased encrustation.

13. The device of claim 8, wherein the at least one surface coating helps to prevent stricture recurrence.

14. The device of claim 1, wherein at least a portion of a surface of at least one of the catheter and the outer sheath includes at least one surface modification.

15. The device of claim 14, wherein the surface is an inner surface of at least one of the catheter and the outer sheath.

16. The device of claim 14, wherein the surface is the outer surface of the outer sheath or an outer surface of the catheter.

17. The device of claim 14, wherein the at least one surface modification is used to affect one or more of adhesion, asepsis, biocompatibility, chemical inertness, degradation, hydrophilicity, lubricity, sterility, surface energy, susceptibility to corrosion, lithogenicity, and thrombogenicity.

18. The device of claim 14, wherein the at least one surface modification inhibits adherence of biological material by providing a texture that is undesirable for adherence.

19. The device of claim 1, wherein at least one of the catheter and the outer sheath is made by including a surface modifying additive to one or more materials used to make the catheter or the outer sheath.

20. The device of claim 1, wherein the expandable dilation member is 10-15 cm in length.

21. The device of claim 1, wherein the device includes radiographic markers to assist in precise localization of the expandable dilation member.

22. The device of claim 1, wherein the expandable dilation member is 3-7 cm in length.

23. The device of claim 1, wherein the expandable dilation member is 5 cm in length.

* * * * *